(12) United States Patent
Hoenig

(10) Patent No.: US 6,508,249 B2
(45) Date of Patent: Jan. 21, 2003

(54) CONNECTING APPARATUS FOR PLACING FLUID FLOW PATHS IN FLUID COMMUNICATION

(75) Inventor: Richard Hoenig, Weare, NH (US)

(73) Assignee: Vital Signs, Inc., Totawa, NJ (US)

( * ) Notice: Subject to any disclaimer, the term of this patent is extended or adjusted under 35 U.S.C. 154(b) by 113 days.

(21) Appl. No.: 09/832,662

(22) Filed: Apr. 11, 2001

(65) Prior Publication Data

US 2002/0148464 A1 Oct. 17, 2002

Related U.S. Application Data

(60) Provisional application No. 60/238,280, filed on Oct. 5, 2000.

(51) Int. Cl.⁷ .................................................. A62B 9/04

(52) U.S. Cl. ................................................. 128/202.27
(58) Field of Search ....................... 128/202.27, 207.14, 128/207.18, 911, 912

(56) References Cited

U.S. PATENT DOCUMENTS

| | | |
|---|---|---|
| 5,121,746 A | 6/1992 | Sikora .................... 128/208.12 |
| D405,522 S | 2/1999 | Hoenig ...................... D24/110 |
| 5,996,639 A | 12/1999 | Gans et al. .................. 138/115 |
| D424,687 S | 5/2000 | Hoenig ...................... D24/110 |

Primary Examiner—William C. Doerrler
Assistant Examiner—Malik N. Drake
(74) Attorney, Agent, or Firm—R. Gale Rhodes, Jr.

(57) ABSTRACT

Connecting apparatus for placing at least one single fluid flow path in fluid communication with at least two single fluid flow paths of a plurality of single fluid flow paths.

18 Claims, 6 Drawing Sheets

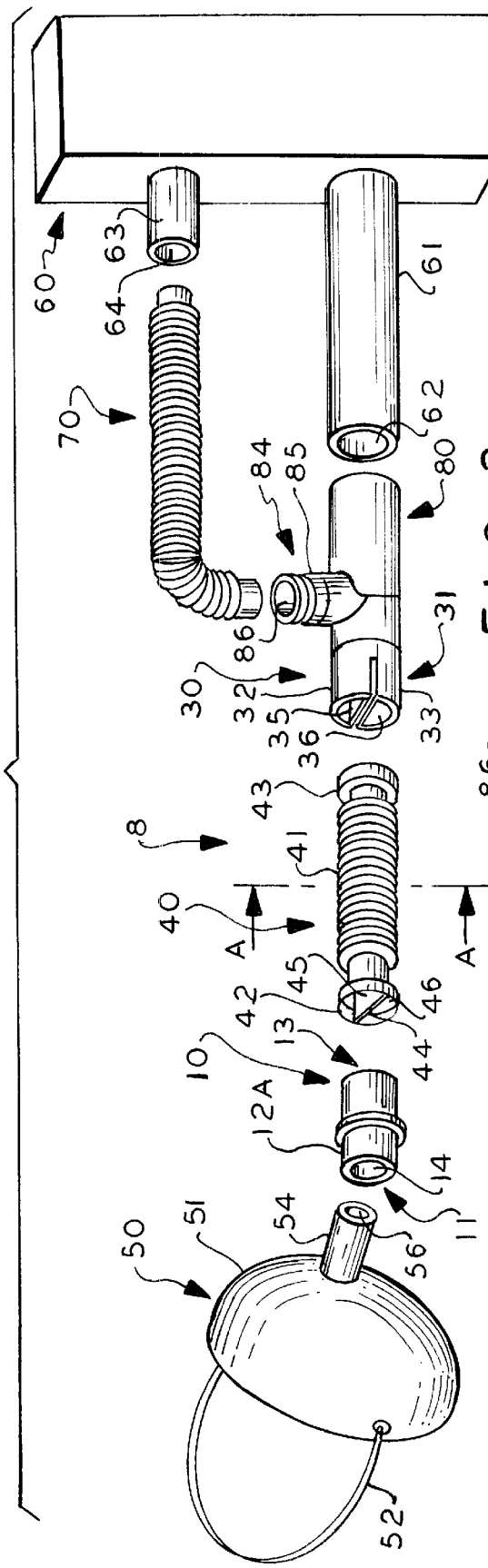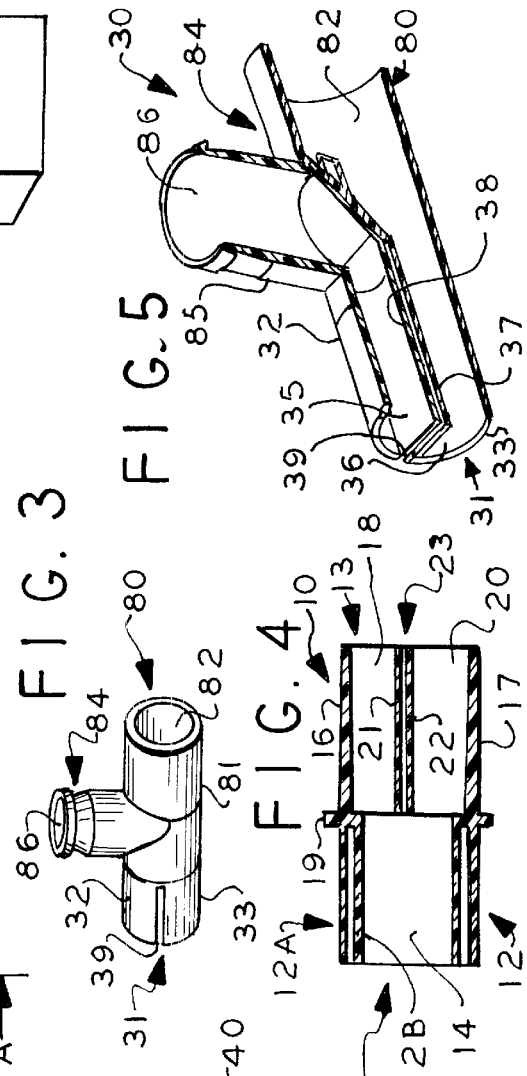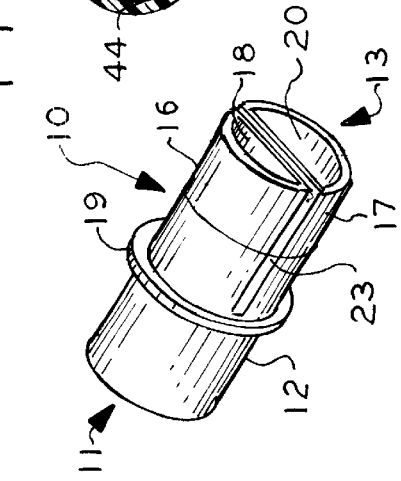

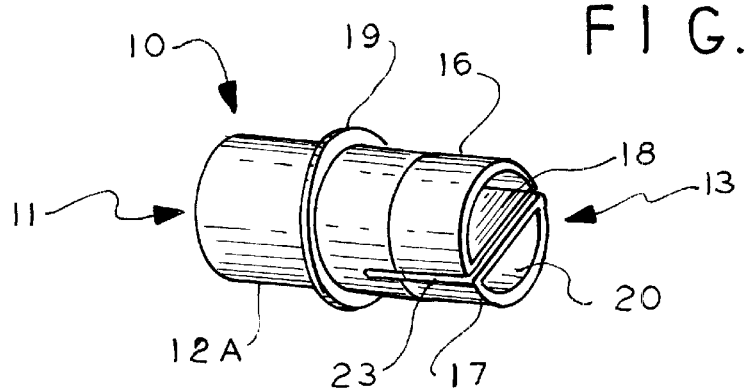
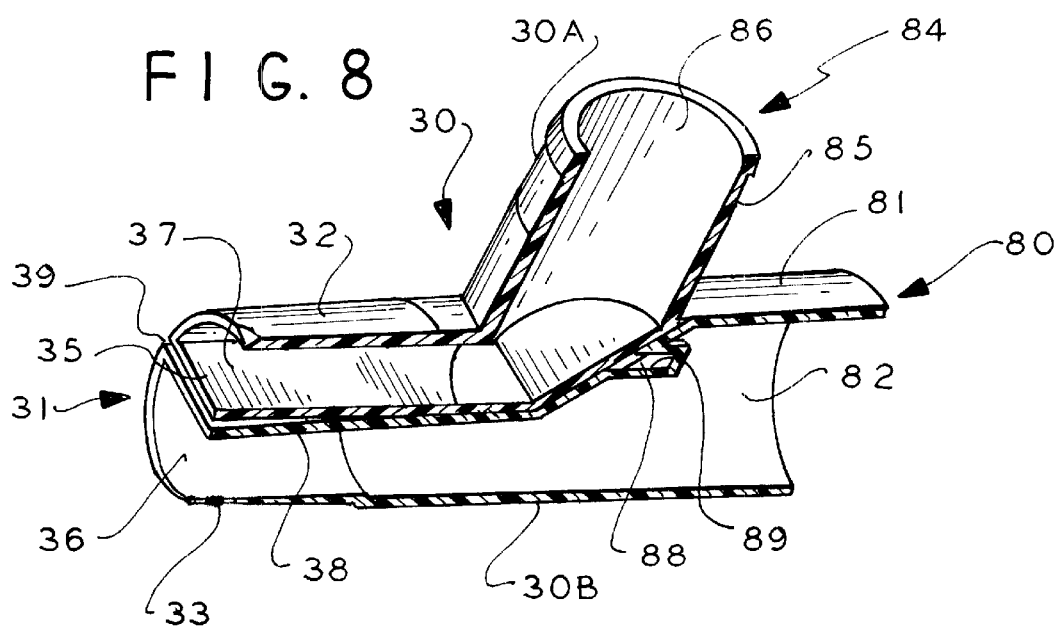
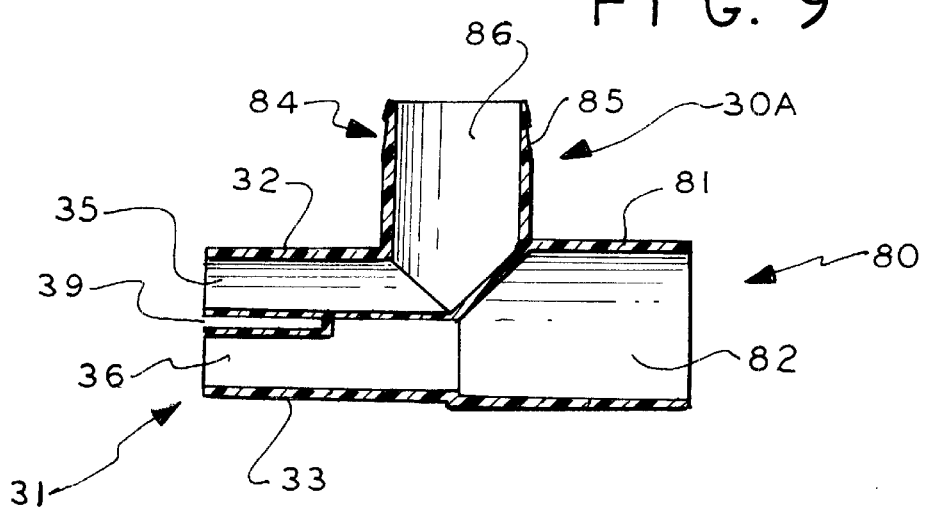

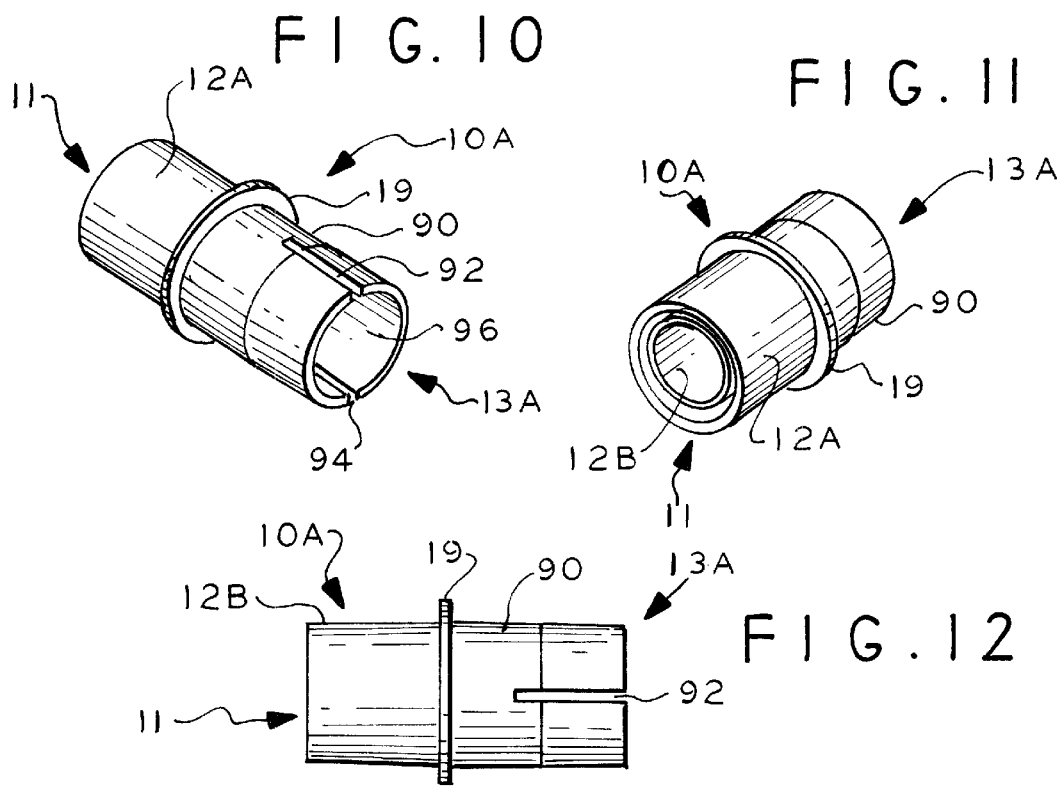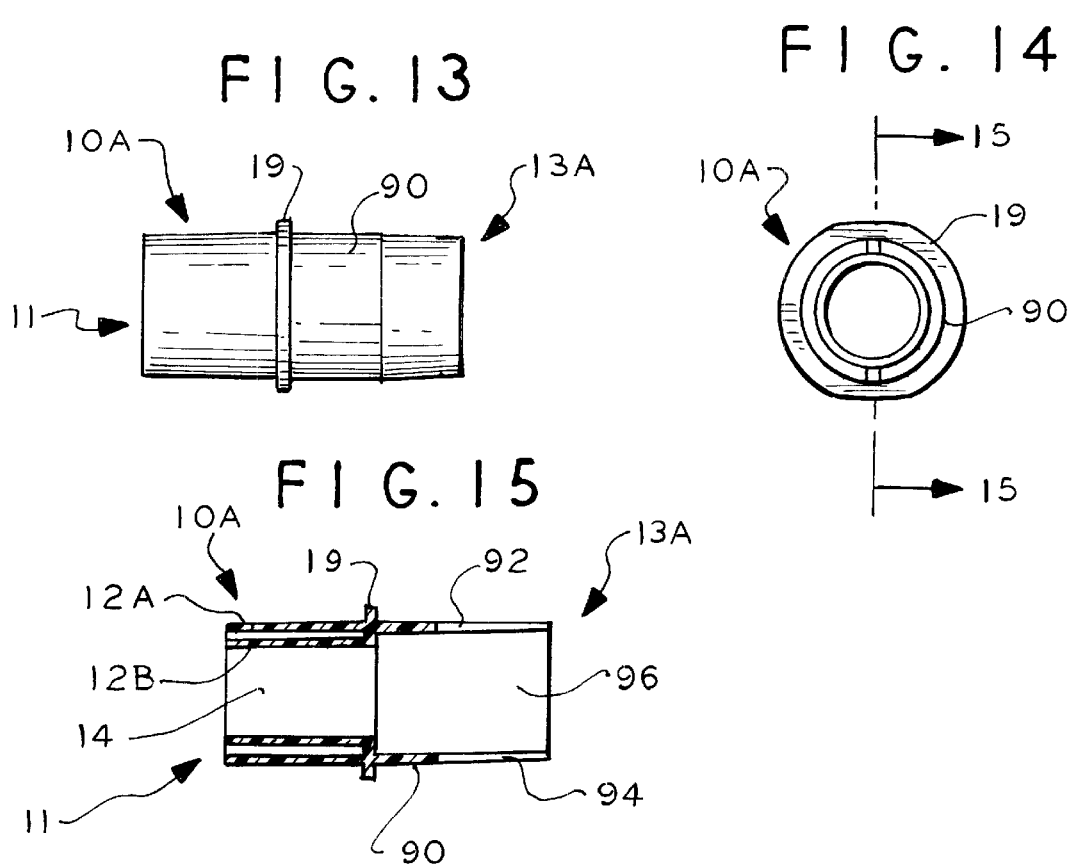

CONNECTING APPARATUS FOR PLACING FLUID FLOW PATHS IN FLUID COMMUNICATION

CROSS-REFERENCE TO RELATED APPLICATIONS

This application claims the benefit of provisional application Ser. No. 60/238,280, filed on Oct. 5, 2000, and assigned to the same assignee as the present application.

BACKGROUND OF THE INVENTION

This invention relates to a multi-lumen hose and multi-lumen hose connecting apparatus. More particularly, this invention relates to multi-lumen hose having a plurality of fluid flow paths and to multi-lumen hose connecting apparatus, or fluid connectors, for connecting the hose to a single flow path and to a plurality of single flow paths. Still more particularly, this invention relates to multi-lumen hose connecting apparatus, or fluid connectors, for connecting multi-lumen hose having a plurality of fluid flow paths to a single fluid flow path and to a plurality of single fluid flow paths.

Still more particularly, this invention relates to connecting apparatus, or fluid connector, for interconnecting a multi-lumen hose and a patient delivery device, such as a face mask or an endotracheal tube (including a pharyngeal mask airway and a laryngeal airway), so that gas, such as anesthesia gas or breathing gas such as air, oxygen or oxygen enriched air, can be communicated through one lumen of the hose to the patient delivery device and thereby to the patient, and so that exhalation gas from the patient can be communicated away from the patient through another lumen of the hose.

Still further, this invention relates to connecting apparatus, or fluid connector, for interconnecting a multi-lumen hose with a gas delivery device, such as an anesthesia machine or breathing gas from a ventilator, or respirator, so that anesthesia gas from such anesthesia machine or breathing gas from the ventilator can be communicated through one lumen of the hose to a patient, and so that exhalation gas from the patient can be communicated away from the patient and through another lumen of the hose to such anesthesia machine or ventilator.

Numerous patient gas delivery devices are known to the art such as, for example and not by way of limitation, face masks and endotracheal tubes. Such face masks and endotracheal tubes typically are provided with a hollow cylindrical member, or hollow cylindrical portion, providing a single fluid flow path through which anesthesia gas or breathing gas is delivered to the patient and through which exhalation gas is communicated away from the patient. Dual lumen hose are known to the art providing a pair of fluid flow paths, one fluid flow path for communicating gas such as anesthesia gas or breathing gas such as oxygen or oxygen enriched air to the patient and the other fluid flow path for communicating exhalation gas away from the patient. Accordingly, there is a need in the art for connecting apparatus for interconnecting the two fluid flow paths provided by the dual lumen hose with the single fluid flow path provided by the patient gas delivery device.

Typical anesthesia machines and ventilators known to the art are provided with two cylindrical members each providing a single fluid flow path, anesthesia gas or breathing gas such as oxygen or oxygen enriched air flows out of one single fluid flow path and exhalation gas from the patient flows into the other single fluid flow path to the anesthesia machine or ventilator. As noted above, dual lumen hose are known to the art for providing one fluid flow path through which anesthesia gas or breathing gas such as oxygen or oxygen enriched air flow to a patient and a second lumen providing a second fluid flow path through which exhalation gas from the patient is communicated away from the patient and to the anesthesia machine or ventilator. Accordingly, there is a need in the art for connecting apparatus for interconnecting the two fluid flow paths provided by the dual lumen hose with the two cylindrical members provided on the anesthesia machine and ventilator each of which provides a single fluid flow path.

U.S. Pat. No. 5,121,746 entitled ANESTHETIC AND RESPIRATOR BREATHING CIRCUIT DEVICE, John R. Sikora inventor, patented Jun. 16, 1992, is incorporated herein by reference as if fully reproduced herein.

U.S. Pat. No. 5,996,639 entitled MULTIPLE COMPARTMENT CORRUGATED HOSE, Leo Gans et al., patented Dec. 7, 1999, is incorporated herein by reference as if fully reproduced herein.

Design Pat. Des. 405,522 and Des. 424,687, patented Feb. 9, 2000 and May 9, 2000, respectively, disclose multiple embodiments of ornamental designs of breathing tubes for conveying oxygen or anesthesia gas to lungs and conveying exhaled gas away from lungs of a patient, Richard Hoenig inventor of both of these design patents, and these design patents are assigned to the same assignee as the present invention; these design patents are incorporated herein by reference as if fully reproduced herein.

SUMMARY OF THE INVENTION

It is the object of the present invention to satisfy the foregoing needs in the art.

Connecting apparatus satisfying such needs and embodying the present invention may include connecting apparatus for connecting a first member or device providing at least one single fluid flow path to a second member or device providing a plurality of single fluid flow paths and for placing the at least one fluid flow path in fluid communication with at least two of the plurality of single fluid flow paths.

DESCRIPTION OF THE DRAWINGS

FIG. 1 is a diagrammatical illustration of an embodiment of connecting apparatus of the present invention including a pair of fluid connectors and a dual lumen hose for interconnecting a face mask with an anesthesia machine or a ventilator;

FIG. 1A is a cross-sectional line taken generally along the line A—A in FIG. 1 in the direction of the arrows;

FIG. 2 is a separate view of one of the connecting apparatus, or fluid connectors, shown in FIG. 1 but rotated 180° in the horizontal with respect to FIG. 1 to better show the end of this fluid connector opposite one end of the dual lumen hose;

FIG. 3 is a separate view of the other one of the connecting apparatus, or fluid connectors shown in FIG. 1, but rotated 180° in the horizontal with respect to FIG. 1 to better show the end of this connecting apparatus or fluid connector facing the anesthesia machine or ventilator;

FIG. 4 is a cross-sectional view of one of the connecting apparatus or fluid connector shown in FIG. 1;

FIG. 5 is a perspective generally vertical cross-sectional view of the other of the connecting apparatus or fluid connector shown in FIG. 1;

FIG. 7 is a perspective view of an alternate embodiment of one of the fluid connectors of the present invention;

FIG. 8 is an enlarged view of the fluid connector shown in FIG. 5 to show the connector in greater detail;

FIG. 9 is a vertical cross-sectional elevational view of an alternate embodiment of the fluid connector shown in FIGS. 1 to 8;

FIG. 10 is a perspective view of an alternate embodiment of the fluid connector shown in FIGS. 1, 2, 4 and 7;

FIG. 11 is another perspective view of the alternate embodiment fluid connector shown in FIG. 10 but rotated approximately 90° with respect thereto.

FIG. 12 is a top view of the fluid connector shown in FIG. 10;

FIG. 13 is a side view of the connector shown in FIG. 12;

FIG. 14 is a right end view of the fluid connector shown in FIG. 13;

FIG. 15 is a vertical elevational view of the fluid connector shown in FIG. 14 taken generally along the line 15—15 in the direction of the arrows;

DESCRIPTION OF THE PREFERRED EMBODIMENT

Figure 6:
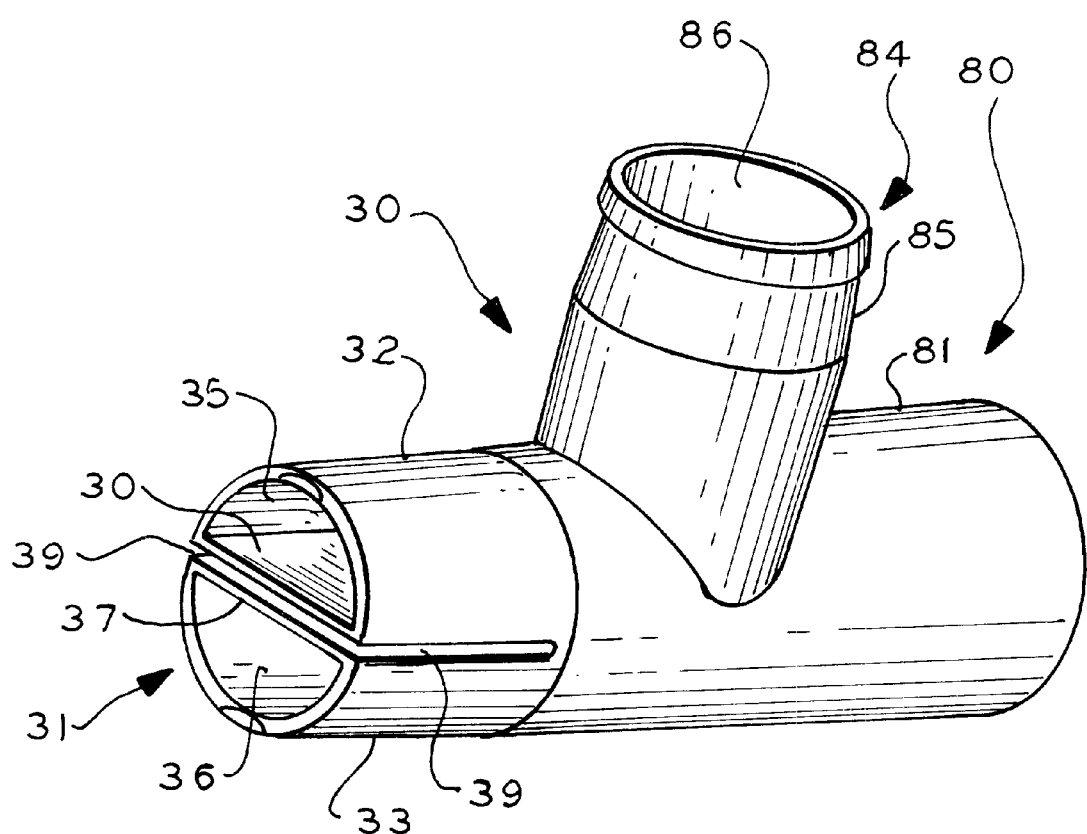
FIG. 6 is an enlarged view of one of the connecting apparatus or fluid connector of the present invention to better show the dual lumen hose connection end.

Referring to FIG. 1, there is shown first connector apparatus embodying the present invention and indicated by general numeral designation 8. The connecting apparatus 8 is for placing a patient's mask indicated by general numerical designation 50 in fluid communication with an anesthesia machine or ventilator indicated by general numerical designation 60. The connecting apparatus 8 may include a first fluid connector indicated by general numerical designation 10, a second fluid connector indicated by general numerical designation 30 and a dual lumen flexible, corrugated hose indicated by general numerical designation 40. The fluid connectors 10 and 30 also comprise embodiments of the present invention. The connecting apparatus 8 may also include a flexible corrugated single lumen hose indicated by general numerical designation 70.

The dual lumen hose 40 of FIG. 1 includes a corrugated outer peripheral wall 41, a pair of opposed end cuffs or end portions 42 and 43 and an inner partition, inner wall or septum 44, note FIG. 1A, dividing the hose into a first lumen 45 providing a first hose or lumen fluid flow path and into a second lumen 48 providing a second hose or lumen fluid flow path.

The mask 50 includes a mask body 51 for being placed over portions of a patient's face, an elastic strap 52 for fastening the mask to the patient's head and an outwardly extending mask tubular member 54 providing a mask single fluid flow path 56 through which anesthesia gas from an anesthesia machine or breathing gas from a ventilator flows to a patient wearing the mask 50 and through which exhalation gas from the patient flows to such anesthesia machine or ventilator.

The anesthesia machine or ventilator 60, FIG. 1, includes a first machine tubular member 61 providing a first machine single fluid flow path 62 through which anesthesia gas or breathing gas flows outwardly and a second machine tubular member 63 providing a second machine single fluid flow path 64 into which exhalation gas from the patient flows into the anesthesia machine or ventilator; it will be understood that the anesthesia machine or ventilator 60 and the tubular members 61 and 63 are shown diagrammatically and not actually in FIG. 1 and that such anesthesia machine or ventilator 60 may be any one of several anesthesia machines or respirators, known to the art; such ventilators are sometimes referred to in the art as respirators.

Referring to FIGS. 1, 2 and 4, the first connecting apparatus or fluid connector 10 includes a first portion or a first end indicated by general numerical designation 11 and a second portion or a second end indicated by general numerical designation 13; the first end 11 comprises a hollow cylinder or tubular member 12 providing a connector single fluid flow path 14 (FIGS. 1 and 4) and the second end 13 comprises or includes a pair of generally parallel hollow or tubular members 16 and 17 each being generally semi-circular in transverse cross-section (FIGS. 2 and 7); the tubular members 16 and 27 providing a pair of connector fluid flow paths 18 and 20, best seen in FIG. 4. As will be best understood from FIG. 4, the tubular members 16 and 17 include opposed and spaced apart flat portions 21 and 22 providing an inwardly extending connector slot 23 therebetween. As will be further understood from FIG. 4, the connector fluid flow path 14 and the connector fluid flow paths 18 and 20 are in fluid or flow communication.

Referring again to FIGS. 1 and 4 and in particular to FIG. 4, it will be generally understood that the first end 11 of the connecting apparatus 10 is comprised of two concentric hollow cylinders or tubular members 12A and 12B. The outer hollow cylinder 12A is dimensioned for sliding sealing engagement into the mask tubular member 54 (FIG. 1) to place the connector single fluid flow path 14 into fluid flow communication with the face mask single fluid flow path 56. The tubular members 16 and 17 comprising the second end 13 of the connecting apparatus 10, note particularly FIGS. 2 and 4, are configured and dimensioned for insertion into the hose lumen 45 and 46 and sliding sealing engagement with the leftward end or end portion of the hose 40 as viewed in FIG. 1 to place the two connector fluid flow paths 18 and 20 provided by the tubular members 16 and 17 of the fluid connector 10 into fluid or fluid flow communication with the two fluid flow paths provided by the hose lumen 45 and 46. As the tubular members 16 and 17 of the fluid connector 10 are inserted, respectively, into the hose lumen 45 and 46, the connector slot 23 provided between the tubular members 16 and 17 receives the outer end portion of the inner wall or septum 44. This interconnection places the mask single fluid flow path 56 into fluid flow communication with the hose or lumen two fluid flow paths provided by the lumen 45 and 46 through the fluid flow path 14 and the fluid flow paths 18 and 20 extending through the connecting apparatus 10. The inner hollow cylinder 12B, FIG. 4, of the fluid connector 10 is dimensioned for sliding sealing engagement and insertion over the outer or proximal end of an endotracheal tube (not shown). It will be understood that the connecting apparatus of the present invention can be used equally well with an endotracheal tube (not shown) and a face mask and that both the endotracheal tube and face mask are referred to in the art as a patient interface device.

As will be further understood from FIGS. 2 and 4, the intermediate portion of the fluid connector 10 is provided with a radially outwardly extending annular rim or ridge 19 which facilitates the gripping of the fluid connector 10 and the insertion of the fluid connector 10 into sealing engagement with the mask 50 and dual lumen hose 40 of FIG. 1.

Referring to FIGS. 1, 3, 5 and 6, the connecting apparatus or fluid connector 30 includes a first end portion or first end, leftward and as viewed in FIG. 1, having the same configuration as the second end 13 of the connecting apparatus 10. The first end of the connecting apparatus 30 is indicated by general numerical designation 31 and includes a pair of generally parallel hollow or tubular members 32 and 33 each being generally semi-circular in transverse cross-section, note FIGS. 1 and 6. The tubular members 32 and 33 provide a pair of connector fluid flow paths 35 and 36 (FIGS. 5 and 6). Similar to the tubular members 16 and 17 of the fluid connector 10, the tubular members 32 and 33 of the fluid connector 30 include a pair of opposed and spaced apart flat portions 37 and 38 (FIGS. 5 and 6) providing an inwardly extending connector slot 39 extending therebetween. Referring further to FIGS. 1, 3, 5 and 8, the tubular hollow members 32 and 33 of the first end 31 of the connecting apparatus 30 are for being inserted into the two lumen 45 and 46 of the hose 40 and placed into sliding sealing engagement with the rightward end of the hose 40 (as viewed in FIG. 1) with the connector slot 39 receiving the end or end portion of the hose inner wall 41. This interconnection places the two fluid flow paths 35 and 36 provided by the tubular members 32 and 33 of the connector 30 in fluid communication respectively with the two fluid flow paths provided by the hose lumen 45 and 46, FIG. 1A.

The second end portion or second end of the connecting apparatus 30 is indicated by general numerical designation 80 and comprises a hollow cylinder or tubular member 81 and providing a connector single fluid flow path 82, best seen in FIGS. 5 and 8, in fluid communication with the connector single fluid flow path 36 provided by the tubular member 33. The end 80 of the fluid connector 30, FIG. 1, is shaped and dimensioned for sliding sealing engagement over and with the outer end of the machine tubular member 61 to connect the fluid connector 30 to the anesthesia machine or ventilator 60 and to place the connector single fluid flow path 82 into fluid communication with the machine single fluid flow path 62.

The intermediate portion of the fluid connector 30 is identified by general numerical designation 84, FIGS. 3, 5 and 6, and comprises a hollow cylinder or tubular member 85 providing a connector single fluid flow path 86 in fluid flow or fluid communication with the single fluid flow path 35 provided by the tubular member 32. From FIG. 1, it will be understood that the leftward end of the single lumen hose 70 is for being placed over and into sliding sealing engagement with the hollow cylinder 85 of the connector intermediate portion 84 (FIG. 5), and the rightward end of the single lumen hose 70 is for being placed over and into sliding sealing engagement with the outer end of the machine tubular member 63, to place the connector single fluid flow path 86 (FIG. 5) in fluid communication with the machine single fluid flow path 64 provided by the machine tubular member 63.

Upon the above-described interconnections of the connecting apparatus or fluid connectors 10 and 30 of the present invention being made, it will be understood that anesthesia gas or breathing gas flows from the anesthesia machine or ventilator 60 through the machine single fluid flow path 62 of the machine tubular member 61, through the fluid flow paths 82 and 36 (FIG. 5) provided by the respective ends 80 and 31 of the connection apparatus 30, through the hose or lumen fluid flow path 46 (FIG. 1A), through the fluid flow path 20 (FIG. 4) provided by the tubular member 17 of the end 13 of the fluid connector 10 and through the fluid flow path 14 provided by the end 11 of the fluid connector 10 and therefrom through the mask single fluid flow path 56 provided by the mask tubular member 54 and into the mask and therefrom to a patient wearing the mask 50. Exhalation gas from a patient wearing the mask 50 flows through the mask single fluid flow path 56 provided by the mask tubular member 54, through the fluid flow path 14 (FIG. 4) provided by the end 11 of the connector apparatus 10, through the fluid flow path 18 provided by the connector apparatus 10 tubular member 16, through the hose or lumen fluid flow path 45 (FIG. 1A), through the fluid flow path 35 (FIG. 5) provided by the first end 31 of the connecting apparatus 30, through the fluid flow path 86 provided by the intermediate portion 84 of the connecting apparatus 30, through the single lumen hose 70 and through the machine single fluid flow path 64 provided by the machine tubular member 63 of the anesthesia machine or ventilator 63 and thereby into such anesthesia machine or ventilator.

As will be understood by those skilled in the anesthesia machine or ventilator art, exhalation gas from a patient wearing the mask 50, FIG. 1, while it can also flow through the fluid path 14 and tubular fluid path 20 of the connector 10, and through the hose lumen 46, and through the single fluid paths 36 and 82 (FIG. 5) provided by the fluid connector 30, and into the machine single fluid flow path 62 provided by the machine tubular member 61 (FIG. 1) such exhalation gas will not enter the anesthesia machine or ventilator 60 due to a valve provided in such machines for preventing entry of patient exhalation gas therein through machine tubular member 61.

It will be understood that the fluid connectors 10 and 30 may be made, by way of example and not by way of limitation, by injection molding and from polypropylene. Referring to FIG. 8, it will be understood that fluid connector 30 may be made in two separate pieces, separate piece 30A and separate piece 30B which are suitably assembled together as shown in FIG. 8 with separate piece 30A being provided with an outwardly extending member 88 for being wedgedly received in a slot 89 provided by separate piece 30B.

An alternate embodiment of the fluid connector 30 is shown in FIG. 9 and indicated by general numerical designation 30A. Fluid connector 30A differs from fluid connector 30, solely, in that fluid connector 30A is formed integrally or in one piece such as, for example, by the above-noted injection molding from polypropylene.

FIGS. 10–14 illustrate an alternate embodiment of the fluid connector 10 of FIGS. 1, 2 and 4 which is indicated by general numerical designation 10A. It will be generally understood that alternate embodiment fluid connector 10A includes an end portion 11 which is the same as the end portion 11 of fluid connector 10 of FIGS. 1, 2 and 4 and is comprised of the same structural elements which perform the same function and hence such structural elements of fluid connector 10A are given the same numerical designations as the corresponding structural elements of fluid connector 10 in FIGS. 1, 2 and 4. However, the end or end portion 13A of fluid connector 10A differs from the end portion 13 of fluid connector 10 in that end portion 13A of fluid connector 10A, note particularly FIGS. 10, 12 and 15, is comprised of a tubular or hollow cylinder member 90 provided with a pair of inwardly extending and diametrically opposed slots 92 and 94. The hollow cylinder 90, note FIG. 15, provides a connector single fluid flow path 96 in fluid communication with the connector single fluid flow path 14 provided by the end 11A of fluid connector 10A. In use, the end portion 11 of the fluid connector 10A is connected to the tubular member 54 of the face mask 50, FIG. 1, in the same manner described above with regard to fluid connector 10. The end 13A or hollow cylinder 90 of the fluid connector 10A is inserted into the hose lumen 45 and 46 (FIG. 1A) and into sliding sealing engagement with the leftward end portion of the hose 40, as viewed in FIG. 1 with the diametrically opposed slots 92 and 94, FIGS. 10, 12 and 15, receiving the leftward end or end portion of the hose inner wall 41. Thereafter, the fluid connector 10A performs the same function as described above for the fluid connector 10.

It will be further understood that additional embodiments of the hose 40, FIG. 1, and the various fluid connectors shown in the drawings and described above, are contemplated by the present invention. For example, the hose 40 of FIG. 1 may be modified to include inner walls of different numbers and shapes as disclosed in FIGS. 4–6 of design patents Des. 405,522 and Des. 424,687 incorporated hereinabove. Consistent with such hose modifications, it will be understood that the end portions of the fluid connectors will be modified accordingly so as to engage the ends of the modified hoses. For example, upon the hose 40 being modified to include the three inner walls shown in FIG. 4 of the incorporated design patterns, the fluid connector 10 of FIG. 2 would be modified to include three generally parallel tubular members having transverse cross-sections shaped complementary to and for insertion into the three lumen provided by the hose embodiment of FIG. 4 of the incorporated design patents. The three tubular members of such modified fluid connector would provide three inwardly extending slots to receive the end portions of the three lumen of such modified hose. The fluid connector 30 shown in FIG. 1 also would be modified to include three inwardly extending axial slots to receive end portions of the three inner walls of the hose 40 upon being modified to include the three inner walls shown in FIG. 4 of the incorporated design patents. Similarly, the generally parallel tubular members 32 and 33 of fluid connector 30 shown in FIG. 1 would be modified to include three generally parallel tubular members complementary in cross-section to and for insertion into the three lumen provided by the three inner walls of the hose 40 upon being modified to include the three inner walls shown in FIG. 4 of the incorporated design patents. Such three tubular members of the modified connector 30 would provide three inwardly extending slots to receive the three end portions of such three inner hose walls.

The first end portion 61 of the fluid connector 60 is for being connected to the tubular member 54 of the face mask 50 (FIG. 1) and the tubular members 65 and 66 of the second end portion of the fluid connector 60 are for being inserted into the lumens 45 and 46 of the rightward end portion of the hose 40 shown in FIG. 1 with the slot 70 receiving the leftward end portion of the inner wall 44 of the hose 40; this places the second end portion 62 of the fluid connector 60 in fluid communication with the dual lumens 45 and 46 of the hose 40.

Figure 16:
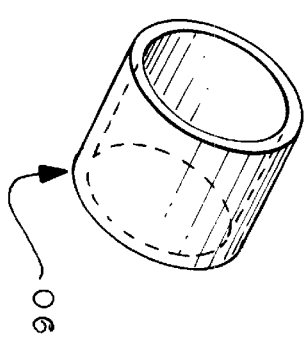
FIG. 16 is a perspective view of a resilient annular seal.

FIG. 16 shows a resilient annular seal identified by general numerical designation 90. The seal 90 may be made of any suitable and commercially available sealing material such as, for example rubber or an elastomer.

Figure 17:
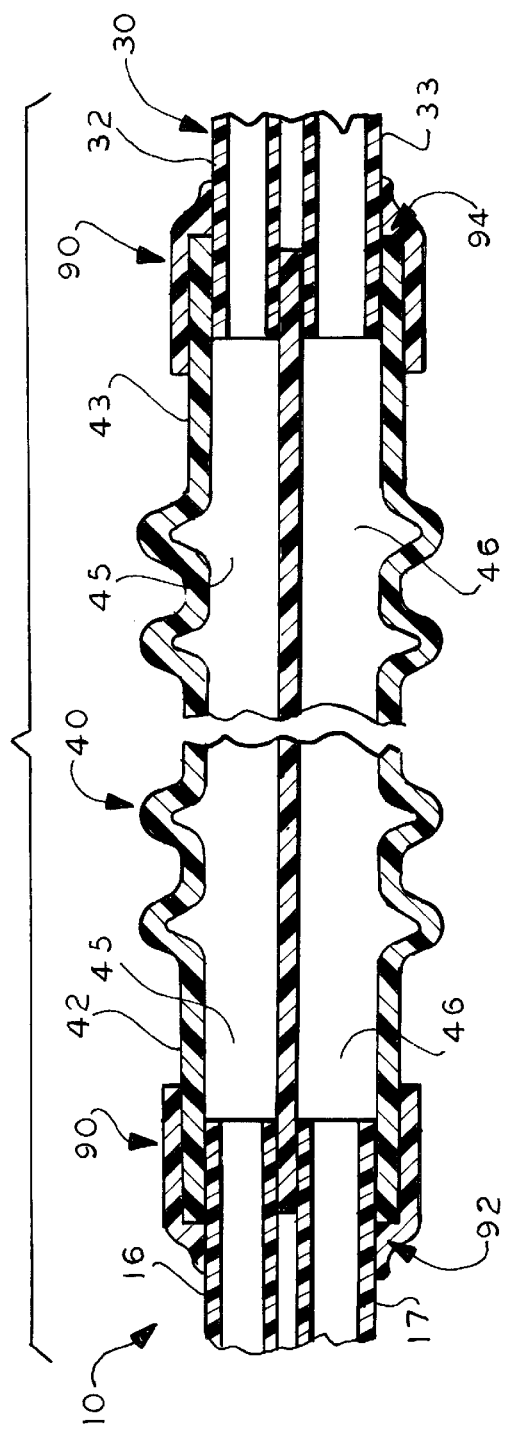
FIG. 17 is a vertical cross-sectional view of two of the seals shown in FIG. 16 in use as part of the connecting apparatus of the present invention.

FIG. 17, the leftward portion, shows the seal 90 surrounding, tightly engaging and further sealing the joint or interface, indicated by general numerical designation 92, between the tubular members 16 and 17 of the fluid connector 10 upon such tubular members being inserted as described above into the lumen 45 and 46 (FIG. 1) of the hose 40. Similarly, FIG. 17, the rightward portion, shows the seal 90 surrounding, tightly engaging and further sealing the joint or interface, indicated by general numerical designation 94, between the tubular members 32 and 33 of the fluid connector 30 upon such tubular members being inserted, as described above, into the lumen 45 and 46 of the hose 40. Further, similarly, upon the hollow cylinder 90 of the alternate embodiment fluid connector 10A (FIG. 10) being inserted, as described above, into the lumen 45 and 46 of the end portion 42 of the hose 40 (FIG. 1), seal 90 surrounds, tightly engages and further seals the joint or interface between hollow cylinder 90 and the hose end portion 42.

Figure 18:
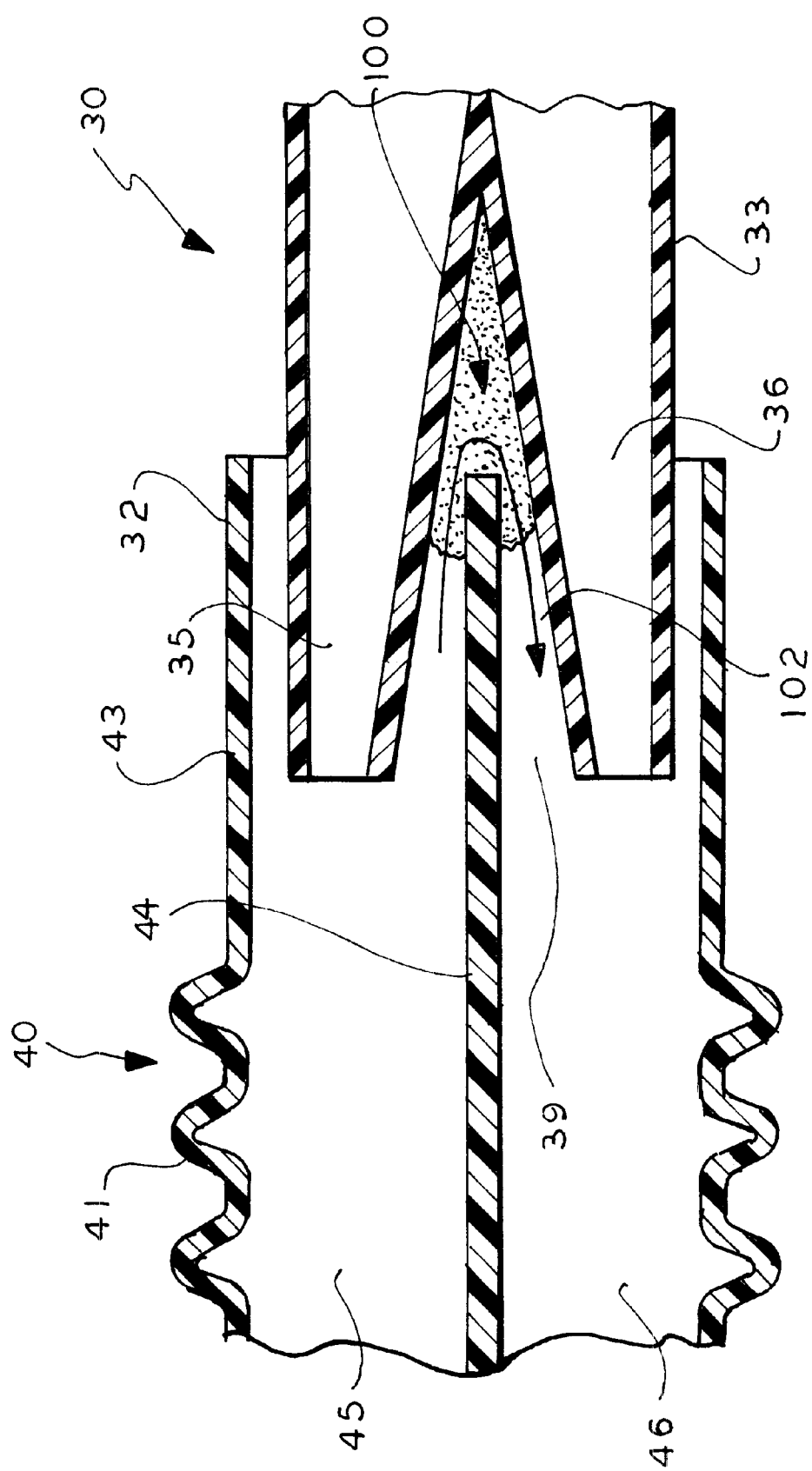
FIG. 18 is a partial enlarged diagrammatical view illustrating how a body of sealing material may be used to prevent gas transfer between exhalation gas and inhalation gas in the fluid connector of the present invention for being connected to an anesthesia machine or ventilator.

As illustrated diagrammatically in FIG. 18, the connecting apparatus of the present invention may include a body of sealing material indicated by general numerical designation 100; for clarity of presentation, the relevant structural elements of the second end portion 43 of the hose 40 (FIG. 1) and the first end or end portion 31 of the fluid connector 30, providing the above-described interconnection between these structural elements, are shown in enlarged view. To prevent cross-contamination between exhalation gas from the patient wearing the mask 50 (FIG. 1) and the inhalation gas, i.e., anesthesia gas or breathing gas, from the anesthesia machine or ventilator 60 (FIG. 1), the body of sealing material 100 may be provided in the slot 39 of the fluid connector 30 and which slot 39, as described above, receives the inner wall of septum 44 of the hose 40. More particularly, it will be understood that upon the body of the sealing material 100 receiving the end portion of the hose inner wall 44 as shown in FIG. 18, carbon dioxide contained in the exhalation gas from the patient and flowing in the hose lumen 45 is prevented from entering into, and thereby contaminating, the anesthesia gas or breathing gas flowing through the fluid flow path 36 of the fluid connector 30 and the hose lumen 46. The possible fluid flow path for such carbon dioxide contamination is illustrated in FIG. 18 by the U-shaped arrow 102. The body of sealing material 100 may be, for example, a body of suitable and commercially available silicone or thermoplastic elastomer.

It will be understood by those skilled in the art that many variations and modifications may be made in the present invention without departing form the spirit and the scope thereof.

What is claimed is:

1. A fluid connector comprising a body including opposed end portions, one of said end portions comprising a first hollow cylinder provided with a plurality of inwardly extending axial slots and the other of said end portions comprising a pair of concentrically disposed cylinders including an inner cylinder in fluid communication with said first hollow cylinder.

2. The fluid connector according to claim 1 wherein said body includes an intermediate portion provided with a radially disposed and outwardly extending generally annular ridge.

3. A fluid connector, comprising:
    a body comprising opposed end portions, one of said end portions comprising a hollow cylinder and the other of said end portions comprising a pair of generally parallel, tubular members each being generally semicircular in transverse cross-section and said tubular members including opposed and spaced apart flat portions providing an inwardly extending slot between said pair of tubular members, said pair of tubular members and said cylinder being in fluid communication.

4. A fluid connector, comprising:
- a body including opposed end portions and an intermediate portion, one of said opposed end portions comprising a pair of substantially parallel tubular members each being generally semi-circular in transverse cross-section and said pair of tubular members including opposed and spaced apart flat portions providing an inwardly extending slot between said pair of tubular members;
- the other of said end portions comprising a first hollow cylinder in fluid communication with one of said tubular members; and
- said intermediate portion comprising an outwardly extending second hollow cylinder in fluid communication with the other of said tubular members, said second hollow cylinder disposed substantially perpendicular to said pair of tubular members and said first hollow cylinder.

5. Connecting apparatus for placing a first single fluid flow path provided by first apparatus in fluid communication with a second single fluid flow path and a third single fluid flow path provided by second apparatus, comprising:
- a multi-lumen hose, a first fluid connector and a second fluid connector;
- said multi-lumen hose including at least one inner wall dividing the interior of said hose into a plurality of lumen through which fluid can flow, said hose including a first end portion and a second end portion and said at least one inner wall including a first end portion and a second end portion;
- said first fluid connector for connecting the first device to said first end portion of said hose to place the first single fluid flow path in fluid communication with at least a first lumen and a second lumen of said plurality of lumen, said first fluid connector provided with at least one inwardly extending first connected slot for receiving said first end portion of said at least one inner wall; and
- said second fluid connector for connecting the second apparatus to said second end portion of said hose to place the second single fluid flow path in fluid communication with said first lumen of said plurality of lumen and for placing the second single fluid flow path in fluid connection with said second lumen of said plurality of lumen, said second fluid connector provided with at least one inwardly extending second slot for receiving said second end portion of said hose.

6. The connecting apparatus according to claim 5 wherein said first fluid connector comprises a body providing a first connector single fluid flow path and including a first portion and a second portion, said first portion for connecting to the first apparatus and said second portion provided with said first connector slot and for being inserted into said first end portion of said hose with said first connector slot receiving said first end portion of said at least one inner wall.

7. Connecting apparatus according to claim 5 wherein said first fluid connector comprises a body providing a first connector single fluid flow path and including a first portion and a second portion, said first portion comprising a hollow cylinder and said second portion comprising a pair of generally parallel tubular members each being generally semi-circular in transverse cross-section and said tubular members including opposed and spaced apart flat portions providing an inwardly extending slot therebetween providing said first connector slot, said pair of tubular members for being inserted into said first end portion of said hose with said first connector slot receiving said first end portion of said at least one inner wall.

8. The connecting apparatus according to claim 5 wherein said second fluid connector comprises a body including opposed end portions and an intermediate portion, one of said opposed end portions comprising a pair of generally parallel tubular members each being generally semi-circular in transverse cross-section and said tubular members including opposed flat portions providing an inwardly extending slot therebetween providing said second connector slot, said pair of tubular members for being inserted into said second end portion of said hose with said second connector slot receiving said second end portion of said inner wall; said other end portion of said pair of opposed end portions comprising a first hollow cylinder in fluid communication with one of said tubular members; and said intermediate portion comprising an outwardly extending second hollow cylinder in fluid communication with the other of said tubular members, said second hollow cylinder disposed substantially perpendicular to said pair of tubular members and said first hollow cylinder.

9. Connecting apparatus for placing an interface single fluid flow path provided by an interface tubular member provided on a patient interface device in fluid communication with a first machine single fluid flow path provided by a first machine tubular member and a second machine single fluid flow path provided by a second machine tubular member provided by an anesthesia machine or a ventilator, comprising:
- a dual lumen hose, a first fluid connector and a second fluid connector;
- said dual lumen hose including an inner wall dividing the interior of said hose into a first lumen and a second lumen for transmitting fluid, each of said lumen being generally semi-circular in transverse cross-section, said hose including a first end portion and a second end portion and said inner wall including a first end portion and a second end portion;
- said first fluid connector comprising a first body providing a first connector single fluid flow path and including opposed end portions, one of said opposed end portions of said first fluid connector comprising a first hollow cylinder for being connected to the interface tubular member to connect said first fluid connector to the interface tubular member and to place the interface single fluid flow path in fluid communication with said first connector single fluid flow path, the other end portion of said pair of opposed end portions comprising a second hollow cylinder provided with a pair of diametrically opposed and inwardly extending connector slots, said second hollow cylinder for being inserted into said first end portion of said hose and into said first lumen and second lumen with said pair of diametrically opposed and inwardly extending connector slots receiving said first end portion of said inner wall to connect said first fluid connector to said first end portion of said hose and to place said first connector single fluid flow path in fluid communication with said first lumen and said second lumen;
- said second fluid connector comprising a second body including opposed end portions and an intermediate portion, one of said opposed end portions of said second fluid connector comprising a first tubular member and a second tubular member, said first tubular member and said second tubular member being generally parallel and each of said first tubular member and second tubular member being generally semi-circular in transverse cross-section, said first tubular member and said second tubular member including opposed flat portions providing an inwardly extending connector slot, said first tubular member for being inserted into said first lumen and said second tubular member for being inserted into said second lumen with said inwardly extending connector slot receiving said second end portion of said inner wall to connect said second fluid connector to said second end potion of said hose and to place said first tubular member in fluid communication with said first lumen and to place said second tubular member in fluid communication with said second lumen;

said other of said opposed end portions of said second fluid connector comprising a third hollow cylinder providing a second connector first single fluid flow path in fluid communication with said first tubular member and said third hollow cylinder for being connected to the first machine tubular member to connect said second fluid connector to the anesthesia machine or ventilator and to place said second connector first single fluid flow path in fluid communication with the first machine single fluid flow path; and said intermediate portion of said second fluid connector comprising an outwardly extending fourth hollow cylinder providing a second connector second single fluid flow path in fluid communication with said second tubular member, said fourth hollow cylinder disposed substantially perpendicular to said first tubular member and said second tubular member and said fourth hollow cylinder and for being connected to said second machine tubular member to place said second connector second single fluid flow path in fluid communication with the second machine single fluid flow path.

10. The connecting apparatus according to claim 9 wherein said connecting apparatus further comprises a single lumen hose interconnected between said fourth hollow cylinder and said second machine tubular member to place said second connector single fluid flow path in fluid communication with said second machine single fluid flow path.

11. The connecting apparatus according to claim 9 wherein said connecting apparatus further comprises a body of sealing material provided in said inwardly extending connector slot for receiving and sealingly surrounding said second end portion of said inner wall thereby preventing fluid communication between said first lumen and said second lumen in said second fluid connector.

12. The connecting apparatus according to claim 9 wherein upon said first hollow cylinder of said first fluid connector being inserted into said first end portion of said hose a first interface is formed between said first hollow cylinder and said first end portion of said hose, and wherein said connecting apparatus further comprises a first resilient annular seal for surrounding, tightly engaging and sealing said first interface in a fluid tight seal, wherein upon said first tubular member and said second tubular member being inserted into said second end portion of said hose a second interface is formed between said first tubular member and said second tubular member and said second end portion of said hose, and wherein said connecting apparatus further comprises a second resilient annular seal for surrounding, tightly engaging and sealing said second interface in a fluid right seal.

13. The connecting apparatus according to claim 12 wherein said connecting apparatus further comprises a single lumen hose interconnected between said third hollow cylinder and said second machine tubular member to place said second connector second single fluid flow path in fluid communication with said second machine single fluid flow path.

14. The connecting apparatus according to claim 12 wherein upon said first tubular member and said second tubular member of said first fluid connector being inserted into said first end portion of said hose a first interface is formed between said first tubular member and said second tubular member and said first end portion of said hose, wherein said connecting apparatus further comprises a first resilient annular seal for surrounding, tightly engaging and sealing said first interface in a fluid tight seal, wherein upon said third tubular member and said fourth tubular member being inserted into said second end portion of said hose a second interface is formed between said third tubular member and said fourth tubular member and said second end portion of said hose, and wherein said connecting apparatus further comprises a second resilient annular seal for surrounding, tightly engaging and sealing said second interface in a fluid tight seal.

15. Connecting apparatus for placing an interface single fluid flow path provided by an interface tubular member provided on a patient interface device in fluid communication with a first machine single fluid flow path provided by a first machine tubular member and a second machine single fluid flow path provided by a second machine tubular member provided by an anesthesia machine or a ventilator, comprising:

a dual lumen hose, a first fluid connector and a second fluid connector;

said dual lumen hose including an inner wall dividing the interior of said hose into a first lumen and a second lumen for transmitting fluid, each of said lumen being generally semi-circular in transverse cross-section, said hose including a first end portion and a second end portion and said inner wall including a first end portion and a second end portion;

said first fluid connector comprising a first body including opposed end portions, one of said opposed end portions of said first fluid connector comprising a first hollow cylinder providing a first connector single fluid flow path and for being connected to the interface tubular member to connect said first fluid connector to the interface tubular member and to place the interface single fluid flow path in fluid communication with said first connector single fluid flow path, the other end portion of said pair of end portions of said second fluid connector comprising a first tubular member and a second tubular member, said first tubular member and said second tubular member being generally parallel and each of said first tubular member and said second tubular member being generally semi-circular in transverse cross-section, said first tubular member and said second tubular member including opposed flat portions providing a first inwardly extending connector slot, said first tubular member for being inserted into said first lumen and said second tubular member for being inserted into said second lumen with said first inwardly extending connector slot receiving said first end portion of said inner wall to connect said first fluid connector to said first end portion of said hose and to place said first tubular member in fluid communication with said first lumen and to place said second tubular member in fluid communication with said second lumen;

said second fluid connector comprising a second body including opposed end potions and an intermediate portion, one of said opposed end potions of said second fluid connector comprising a third tubular member and a fourth tubular member, said third tubular member and said fourth tubular member being generally parallel and each of said first tubular member and said second tubular member being generally semi-circular in transverse cross-section, said third tubular member and said fourth tubular member including opposed flat portions providing a second inwardly extending connector slot, said fourth tubular member for being inserted into said first lumen and said fourth tubular member for being inserted into said second lumen with said second inwardly extending connector slot receiving said second end portion of said inner wall to connect said second fluid connector to said second end portion of said hose and to place said third tubular member in fluid communication with said first lumen and to place said fourth tubular member in fluid communication with said second lumen;

said other of said opposed end portions of said second fluid connector comprising a second hollow cylinder providing a second fluid connector first single fluid flow path in fluid communication with said third tubular member and said second hollow cylinder for being connected to the first machine tubular member to connect said second fluid connector to the anesthesia machine or ventilator and to place said second connector first single fluid flow path in fluid communication with the first machine single fluid flow path; and said intermediate portion of said second fluid connector comprising an outwardly extending third hollow cylinder providing a second connector second single fluid flow path in fluid communication with said fourth tubular member, said third hollow cylinder disposed substantially perpendicular to said second tubular member and said fourth tubular member and said third hollow cylinder and for being connected to said second machine tubular member to place said second connector second single fluid flow path in fluid communication with the second machine single fluid flow path.

16. The connecting apparatus according to claim 15 wherein said connecting apparatus further comprises a body of sealing material provided in said inwardly extending connector slot for receiving and sealingly surrounding said second end portion of said inner wall thereby preventing fluid communication between said first lumen and said second lumen in said second fluid connector.

17. A fluid connector for connecting a device providing at least one single fluid flow path to an end portion of a multi-lumen hose including a plurality of inner walls disposed radially with respect to each other and dividing the interior of the hose into a plurality of lumen and providing a plurality of end portions, comprising:

a body providing at least one connector single fluid flow path and including a first portion and a second portion;

said first portion for connecting to the device; and said second portion including slot means and for connecting to the end portion of the multi-lumen hose, said slot means comprising a plurality of inwardly extending axial slots disposed radially, equal in number and complementary to and for receiving the plurality of end portions of the plurality of inner walls.

18. A fluid connector for connecting a device providing at least one single fluid flow path to an end portion of a multi-lumen hose including a single inner wall dividing the interior of the multi-lumen hose into a pair of lumen each generally semi-circular in transverse cross-section, the single inner wall having an end portion, comprising:

a body providing at least one connector single fluid flow path and including a first portion and a second portion;

said first portion for connecting to the device; and said second portion comprising a pair of generally parallel tubular members each generally semi-circular in transverse cross-section and providing a space therebetween comprising slot means, said tubular members for being inserted into the pair of lumen and said space for receiving the end portion of the single inner wall to connect said second portion to the end portion of the multi-lumen hose to place the pair of lumen in fluid communication with the at least one single fluid flow path.

* * * * *